(12) United States Patent
Alotaibi

(10) Patent No.: US 9,072,575 B1
(45) Date of Patent: Jul. 7, 2015

(54) DENTAL IMPLANT ANGLE MEASUREMENT DEVICE

(71) Applicant: KING SAUD UNIVERSITY, Riyadh (SA)

(72) Inventor: Hanan Nejer Sahil Alotaibi, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 14/497,288

(22) Filed: Sep. 25, 2014

(51) Int. Cl.
*A61C 19/04* (2006.01)
*A61C 8/00* (2006.01)

(52) U.S. Cl.
CPC ............... *A61C 19/04* (2013.01); *A61C 8/0089* (2013.01)

(58) Field of Classification Search
CPC .............................. A61C 19/04; A61C 8/0089
USPC ................. 433/72; 33/513–515; 600/590
See application file for complete search history.

(56) References Cited

U.S. PATENT DOCUMENTS

| | | | |
|---|---|---|---|
| 1,856,779 A | 5/1932 | Montelius | |
| 2,265,893 A | 12/1941 | Bruehl | |
| 2,491,136 A | 12/1949 | Salzmann | |
| 3,229,372 A * | 1/1966 | Quashnock et al. | ............ 33/471 |
| 5,078,600 A | 1/1992 | Austin | |
| 6,030,219 A | 2/2000 | Zuest et al. | |
| 6,048,322 A | 4/2000 | Kushida | |
| 6,299,447 B1 | 10/2001 | Zuest et al. | |
| 6,945,779 B2 | 9/2005 | Richmond | |
| 8,347,517 B2 | 1/2013 | Polei | |
| 2012/0028213 A1 | 2/2012 | Meitner | |

OTHER PUBLICATIONS

"Locator Overdenture Implant System," Zest Anchors, Inc., retrieved on Mar. 7, 2014, 8 pages.
"Locator Parallel Post," Zest Anchors, Inc., retrieved on Mar. 7, 2014, 1 page.
"Locator implant attachment system," Thommen Medical, Feb. 13, 2014, 20 pages.
"Angle Measurement Guide, Final PKG," Zest Anchors, Inc., Feb. 13, 2014, 1 page.
"Locator™ root attachment Quick reference Guide," Zest Anchors, Inc., retrieved Apr. 14, 2014, 2 pages.

* cited by examiner

*Primary Examiner* — Heidi M Eide
(74) *Attorney, Agent, or Firm* — Richard C Litman

(57) ABSTRACT

A dental implant angle measurement device for measuring angular difference includes a reference member that can be engaged with a reference dental component. An elongate member is attached perpendicular to the reference member and a measuring member is movably positioned along the elongate member. The measuring member can be aligned with a target dental component and further includes a base member and an angular indicator. The angular indicator can have gradations and indicia to indicate an angular difference between an axis passing through the reference dental component and an axis passing through the target dental component that the measuring member is aligned with. The target dental component is positioned in the mouth of the patient or in a cast. A stopping member is also positioned with the elongate member to restrict movement of the measuring member in relation to the elongate member.

13 Claims, 5 Drawing Sheets

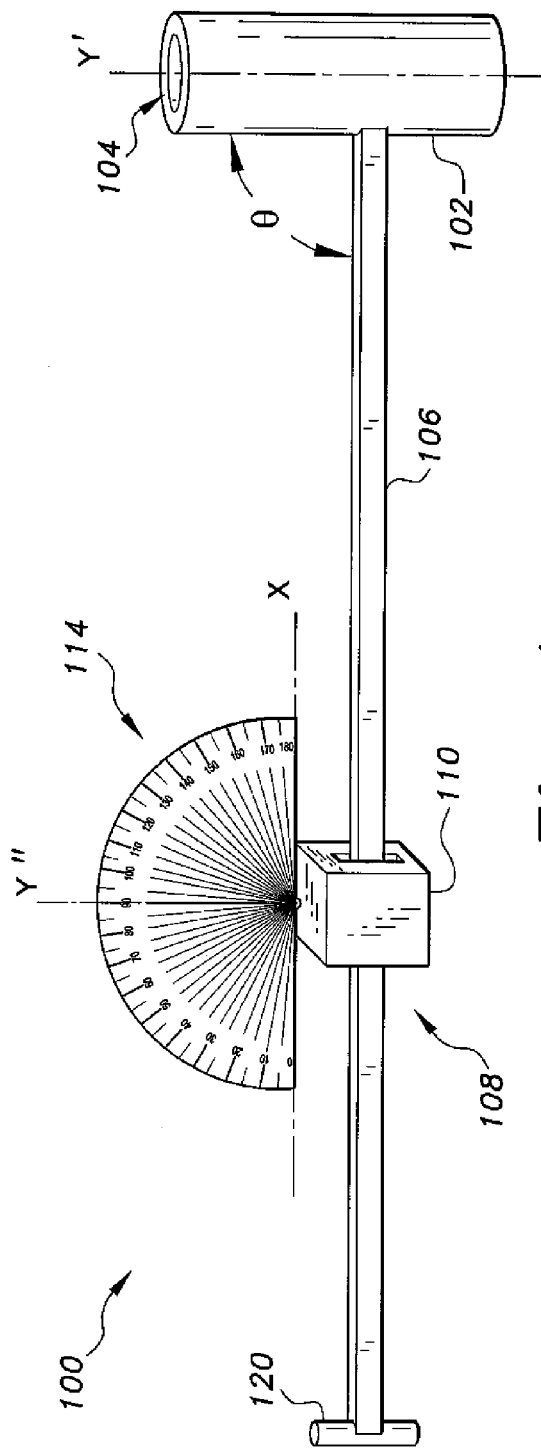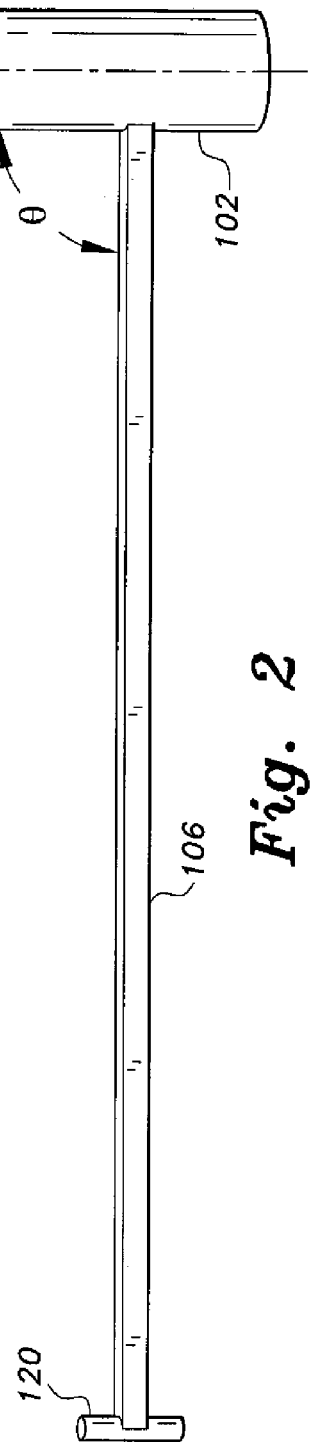

DENTAL IMPLANT ANGLE MEASUREMENT DEVICE

BACKGROUND OF THE INVENTION

1. Field of the Invention

The present invention relates to dental instruments, and particularly to a dental implant angle measurement device.

2. Description of the Related Art

Patients suffering from oral issues, such as edentulous patients, can seek treatment in various forms, such as the use of dental prosthetics. One possible form of treatment involves the use of a crown prosthetic in conjunction with the patient's teeth. Another possible form of treatment involves the use of a denture prosthetic, which is considered a successful treatment modality. When treatment involves the use of a prosthetic, the comfort of the patient and the retention of the prosthetic can be enhanced by incorporating an attachment system in conjunction with the prosthetic.

Examples of prosthetic attachment systems can include the use of a dental implant placed within the oral cavity of the patient. Various features of these dental implants can include external threads that are placed into contact with the bone of the patient, such as the jaw bone, and that can be also placed at an area where the process of osseointegration will occur. The dental implants can also include internal threads within the body of the implant for attachment to other dental components and/or instruments.

Different prosthetic treatment options can be attached to the implants, such as the single crown that can be attached to the implant using a prosthetic screw, or a fixed partial denture that can be fabricated onto two implants and stabilized by screws. Another form of prosthetic treatment which can be attached using dental implants is an over denture that can be attached to the implants and can also be placed in conjunction with an inner surface of a prosthodontics appliance, such as a complete denture, which can enhance retention inside the patient's mouth.

When two or more dental implants are used in the attachment system, success of the treatment can depend upon parallelism between the dental implants. Parallelism can be defined when a vertical axis of one implant is parallel or near parallel to a vertical axis of another implant. If parallelism is established between the two implants this can allow for proper component selection by a user, such as a dentist, and can also help to anticipate the amount of postoperative care that a patient can need. For example, by having parallelism between the dental implants, a proper dental component, such as an accurate male replacement retention liner, can be selected for the implant.

If the dental implants do not have parallelism between them, the operator can select a proper dental component to compensate for the misalignment by using a specially designated dental component, such as nylon band, designated to compensate for the misalignment. Parallelism between the dental implants should be established early during the surgical phase of implant placement. However, if parallelism between the dental implants cannot be determined during surgery for any reason, then parallelism should be determined after surgery is completed.

In measuring parallelism, current dental implant angle measurement devices use a vertical plane perpendicular to a horizontal plane of the implant as a reference, which can allow for a trajectory measurement of up to 25 degrees in both directions. However, the vertical plane that current dental implant angle measurement devices are using as a starting point is not necessarily accurate. Also, accuracy can be relatively easily affected by such factors like the patient's head tilt or by the judgment of the operator who is taking the measurement. Any inaccuracy in the measurements can affect the selection of proper components, such as a retention liner, used in the attachment system.

Thus, it is desirable for a dental implant angle measurement device that can provide an accurate measurement of parallelism, as can take into consideration external factors, such as the patient's head tilt or the actions of the operator.

Thus, a dental implant angle measurement device addressing the aforementioned problems is desired.

SUMMARY OF THE INVENTION

Embodiments of a dental implant angle measurement device are provided. The dental implant angle measurement device includes a reference member that can be engaged with a reference dental component, the reference dental component positioned in a mouth of a patient or in a cast. The dental implant angle measurement device further includes an elongate member attached perpendicular or substantially perpendicular to the reference member and a measuring member movably positioned along the elongate member that can be aligned with a target dental component. The measuring member further includes a base member and an angular indicator, with the angular indicator having one or more of gradations and indicia to indicate an angular difference between an axis passing through the reference dental component and an axis passing through the target dental component that the measuring member is aligned with. The target dental component is positioned in the mouth of the patient or in a cast. A stopping member is also positioned with the elongate member to restrict movement of the measuring member in relation to the elongate member.

These and other features of the present invention will become readily apparent upon further review of the following specification and drawings.

BRIEF DESCRIPTION OF THE DRAWINGS

FIG. 1 is a front view of an embodiment of a dental implant angle measurement device according to the present invention.

FIG. 2 is a front view of an embodiment of a reference member, an elongate member, and a stopping member of an embodiment of a dental implant angle measurement device according to the present invention.

Unless otherwise indicated, similar reference characters denote corresponding features consistently throughout the attached drawings.

DETAILED DESCRIPTION OF THE PREFERRED EMBODIMENTS

Figure 4A:
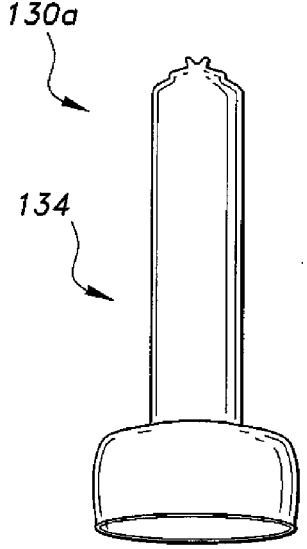
FIG. 4A is a front view of a prior art post of a dental component to which embodiments of a dental implant angle measurement device according to the present invention can be applied.
Figure 4B:
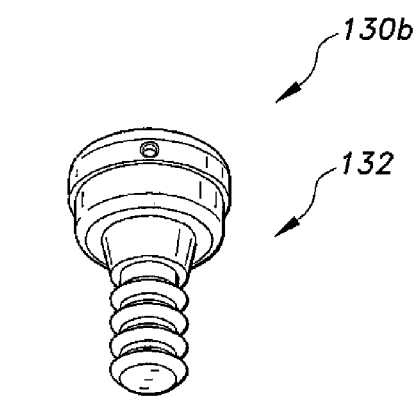
FIG. 4B is a front view of a prior art implant of a dental component to which embodiments of a dental implant angle measurement device according to the present invention can be applied.
Figure 5A:
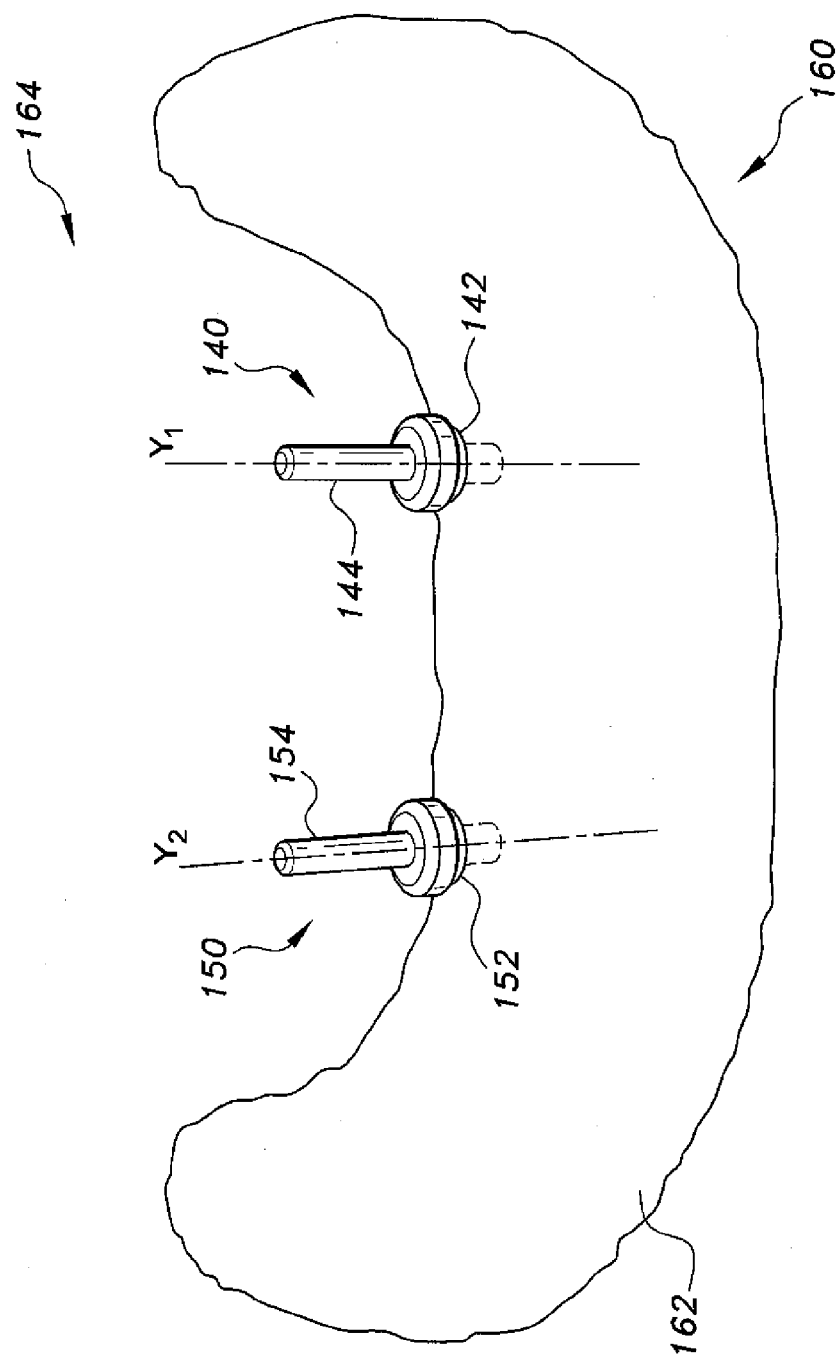
FIG. 5A is an environmental view of a reference dental component and a target dental component positioned in relation to a mouth of a patient according to the present invention.
Figure 5B:
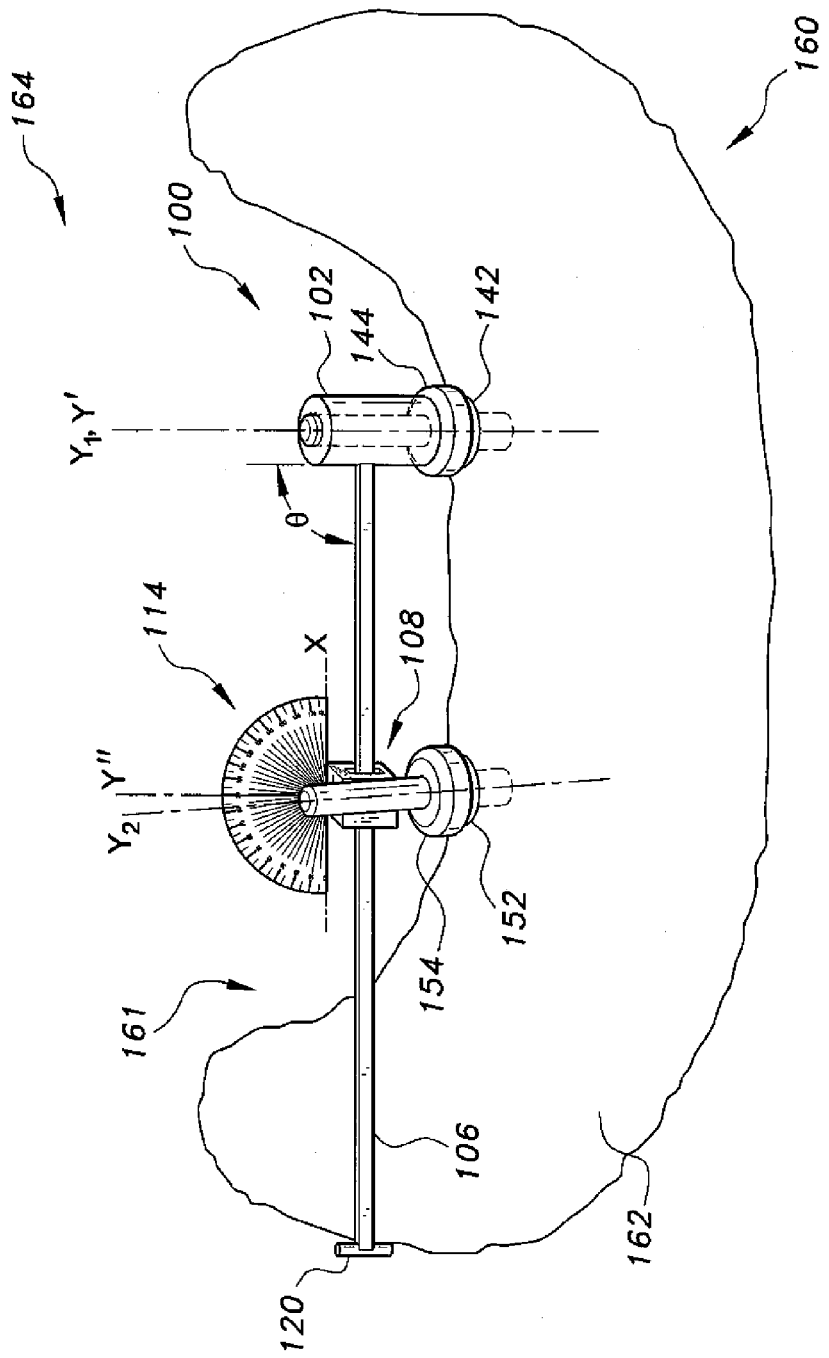
FIG. 5B is an environmental view of an embodiment of dental implant angle measurement device positioned in relation to a mouth of a patient according to the present invention.
Figure 5C:
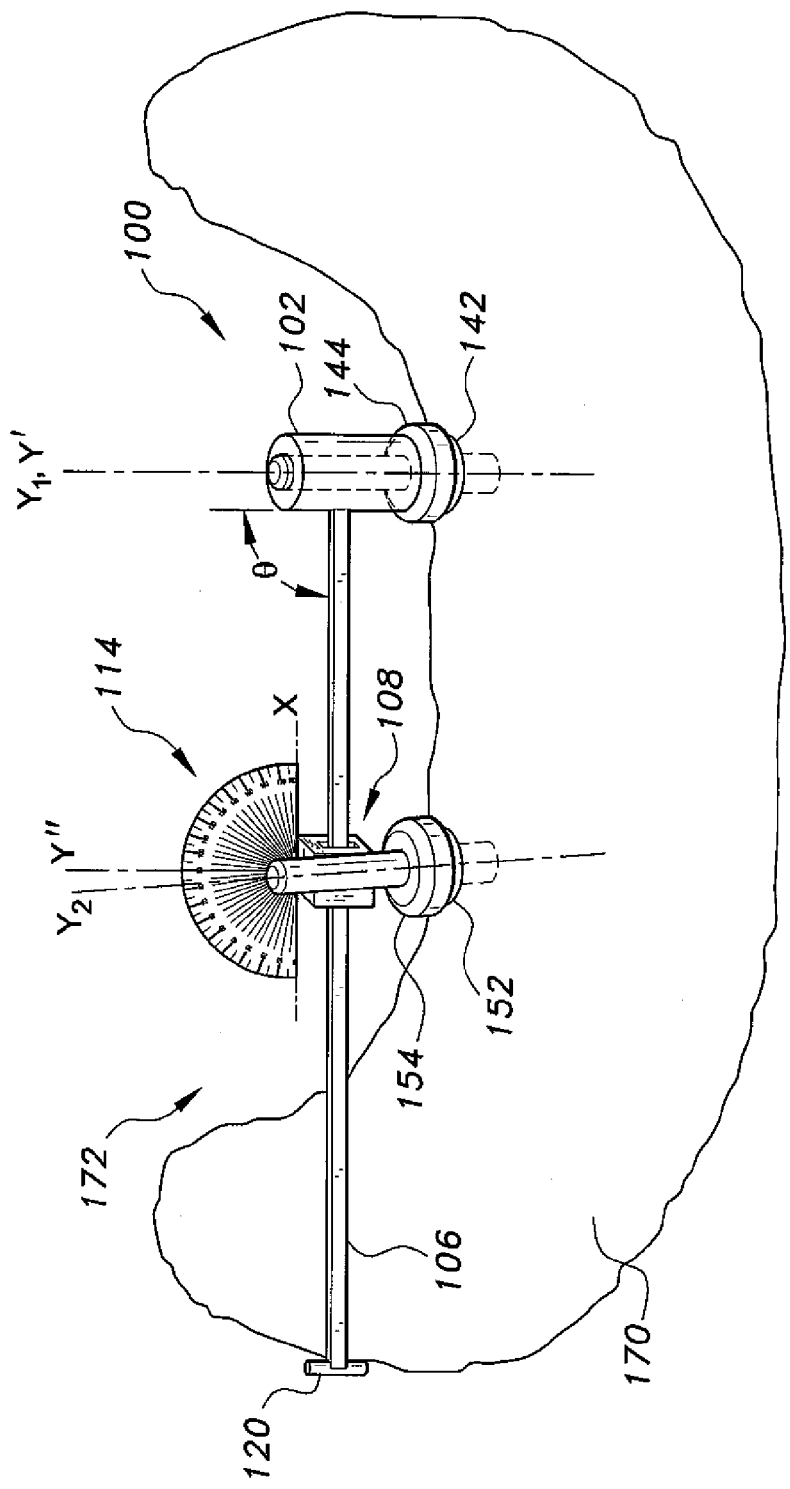
FIG. 5C is an environmental view of an embodiment of a dental implant angle measurement device positioned in relation to a cast, the cast including a reference dental component and a target dental component according to the present invention.

Referring to FIGS. 1-3 and 5A-5C, embodiments of dental implant angle measurement device 100 are shown. Also, FIGS. 4A and 4B illustrate a post and an implant of a dental component to which embodiments of a dental implant angle measurement device, such as the dental implant angle measurement device 100, can be applied. The dental implant angle measurement device 100 has a reference member 102 that includes a lumen 104 and a vertical axis Y'. The lumen 104 of the reference member 102 is adapted to receive and engage a reference dental component 140 that is adapted to be positioned in a mouth 160 of a patient, as shown in FIGS. 5A and 5B, or that is adapted to be positioned in a cast 170, such as a stone cast of a portion of a patient's mouth, for example as shown in FIG. 5C. Therefore, if the reference dental component 140 is placed in the mouth 160 of the patient, the reference member 102 typically should have dimensions that allow for the reference member 102 to be positioned in the patient's mouth 160, such as shown in FIG. 5B. For example, the reference member 102 can be 7 millimeters (mm) long and the lumen 104 of the reference member 102 can have a diameter of 3 mm. Further, the reference member 102 can have a wall thickness of 2 mm, for example. However, the dimensions of the reference member 102 can be of various suitable dimensions, as can depend on the use or application, and should not be construed in a limiting sense.

An elongate member 106 of the dental implant angle measurement device 100 is positioned substantially perpendicular or perpendicular to and in conjunction with the reference member 102, as shown in FIG. 2. The elongate member 106 can have various suitable dimensions, such as dimensions that can allow for the elongate member 106 to be positioned in a patient's mouth 160, as shown in FIG. 5B, or can allow for the elongate member 106 to be positioned in relation to the cast 170, as shown in FIG. 5C, for example. The elongate member 106 can have a square cross section of 2 mm×2 mm and can have a length of 80 mm, for example. However, the dimensions of the elongate member 106 can be of various suitable dimensions, as can depend on the use or application, and should not be construed in a limiting sense.

A target dental component 150, similar to the reference dental component 140, can be positioned in the patient's mouth 160, or can be positioned in the cast 170, such as a stone cast. Also, the length of the elongate member 106 should be long enough to accommodate various possible distance between the reference dental component 140 and a target dental component 150, such as when positioned in the patient's mouth 160, as shown in FIG. 5B, for example. Also, the elongate member 106 should be long enough to accommodate the distance between the reference dental component 140 and the target dental component 150 when both are positioned in the cast 170, as shown in FIG. 5C, for example.

The elongate member 106 can be perpendicularly or substantially perpendicularly positioned at a suitable height in relation to and in conjunction with the reference member 102, such as being positioned at suitable location above an inferior border of the reference member 102 as, for example, at a location 2 mm above the inferior border of the reference member 102, the inferior border of the reference member 102 being located adjacent a base of a post 144 of the reference dental component 140, when the reference member 102 is positioned in engaging relation with the reference dental component 140, for example.

By having the elongate member 106 positioned perpendicular or substantially perpendicular to and in conjunction with the reference member 102, an angle θ is formed between the reference member 102 and the elongate member 106 at a junction where the elongate member 106 is positioned perpendicular or substantially perpendicular to the reference member 102. The angle θ is 90 degrees or about 90 degrees, so that the perpendicular or substantially perpendicular position is maintained between the reference member 102 and the elongate member 106, for example.

The 90 degrees or about 90 degrees angle θ can assist in ensuring parallelism in relation to dental angle implant measurement, such that an angle of a target dental component relative to the reference dental component 140 can be determined with relative high accuracy, for example. The angle measurement utilizing the 90 degrees or about 90 degrees angle θ can assist in enabling such relatively high accurate angle measurement in that such design takes into consideration a concept that a plurality of parallel lines should not cross. In this regard, a 90-degree perpendicular line or a substantially perpendicular line X, such as corresponding to the X axis in the FIGS. 1, 3, 5B and 5C, drawn on one of the plurality of parallel lines, for example, parallel lines that are formed from the Y' and Y" axes shown in FIG. 1, and the perpendicular line X is extended to another parallel line, then this drawn perpendicular line X angle between the first parallel line Y' and the second parallel line Y" should still be 90 degrees or substantially 90 degrees.

Such concept of parallelism between a plurality of parallel lines can be important in enabling a relatively successful securement of a dental prosthetic using dental components, such as prior art dental components 130a and 130b, as shown in FIGS. 4A and 4B, or the dental components shown in FIGS. 5A, 5B and 5C, such as the reference dental component 140 and the target dental component 150. The types of dental prosthetics that can be secured by dental components 130a and 130b and/or the reference dental component 140 and/or the target dental component 150 can include a single crown, a fixed partial denture that can be fabricated onto two implants and stabilized by screws, or an over denture that can be placed in conjunction with an inner surface of a prosthodontics appliance, such as a complete denture, for example.

The dental components 130a and 130b are typically combined to form a dental component as can be implanted in a patient. In this regard, the dental component 130a includes a post 134. The post 134 can be placed in conjunction with the other dental component 130b that includes an implant 132. Common types of dental components, such as can include the dental components 130a and 130b include LOCATOR® branded products by Zest Anchors, Inc., for example.

Similar to the dental components 130a and 130b, the reference dental component 140 includes a post 144 that is in conjunction with an implant 142 and the target dental component 150 also includes a post 154 that is in conjunction with an implant 152, as shown in FIGS. 5A, 5B and 5C. The implant 142 of the reference dental component 140 and the implant 152 of the target dental component 150 are adapted to be positioned in a portion of the patient's mouth 160, for example an anterior portion or part 161 of an oral cavity 164. The implant 142 of the reference dental component 140 and the implant 152 of the target dental component 150 can also include internal threads within the body of the implant 142 or the implant 152 for attachment to other dental components and/or instruments.

The post 144 of the reference dental component 140 and the post 154 of the target dental component 150 are adapted to securely position the implant 142 of the reference dental component 140 and the implant 152 of the target dental component 150 in the portion of the patient's mouth 160, such as positioned in the upper or lower jaw bone 162 of a patient, or positioned in the cast 170, for example. Thus, the dental implant angle measurement device 100 is adapted to be positioned within the oral cavity 164, such as the anterior portion or part 161 of the oral cavity 164 of the patient's mouth 160. Areas of the mouth 160 can include the upper or lower jaw, such as the lower mandibular arch or an area where the process of osseointegration can occur, for example.

The reference dental component 140 and the target dental component 150 are also both adapted to be positioned in the cast 170 such as a stone cast, as illustrated in FIG. 5C, for example. Therefore, the dental implant angle measurement device 100 is also adapted to be positioned for use in angle measurement in relation to the reference dental component 140 and the target dental component 150, when positioned in conjunction with a cast, such as a stone cast, as the cast 170 illustrated in FIG. 5C, for example.

When two or more dental components are used to secure a dental prosthetic, such as the reference dental component 140 and the target dental component 150, the axis $Y_1$ of the reference dental component 140 should be parallel or near parallel to the axis $Y_2$ of the target dental component 150. The parallelism or substantial parallelism between the $Y_1$ and $Y_2$ axes should be established early during the surgical phase of implant placement, but if this cannot be accomplished during the surgery for any reason, then the dental implant angle measurement device 100 can be used to measure the angular difference between the reference dental component 140 and the target dental component 150, after implantation, such as in the upper or lower jaw bone 162 of a patient, for example. By having parallelism or substantial parallelism between the reference dental component 140 and the target dental component 150, a user, such as a dentist, can be assisted in selecting a proper component to be used with the dental prosthetic and can also help to anticipate the amount of postoperative care that the patient likely will need, for example.

The dental implant angle measurement device 100 further includes a measuring member 108. The measuring member 108 is movably positioned in conjunction with the elongate member 106 to selectively position the measuring member 108 along the elongate member 106 so that the measuring member 108 can be in an aligned relation, such as aligned or substantially aligned, with the target dental component 150, as shown in FIGS. 5B and 5C. Since the reference member 102 and the elongate member 106 are positioned in perpendicular or substantially perpendicular relation to one another, an angle of the target dental component 150 relative to the reference dental component 140 can be determined by the measuring member 108.

Figure 3:
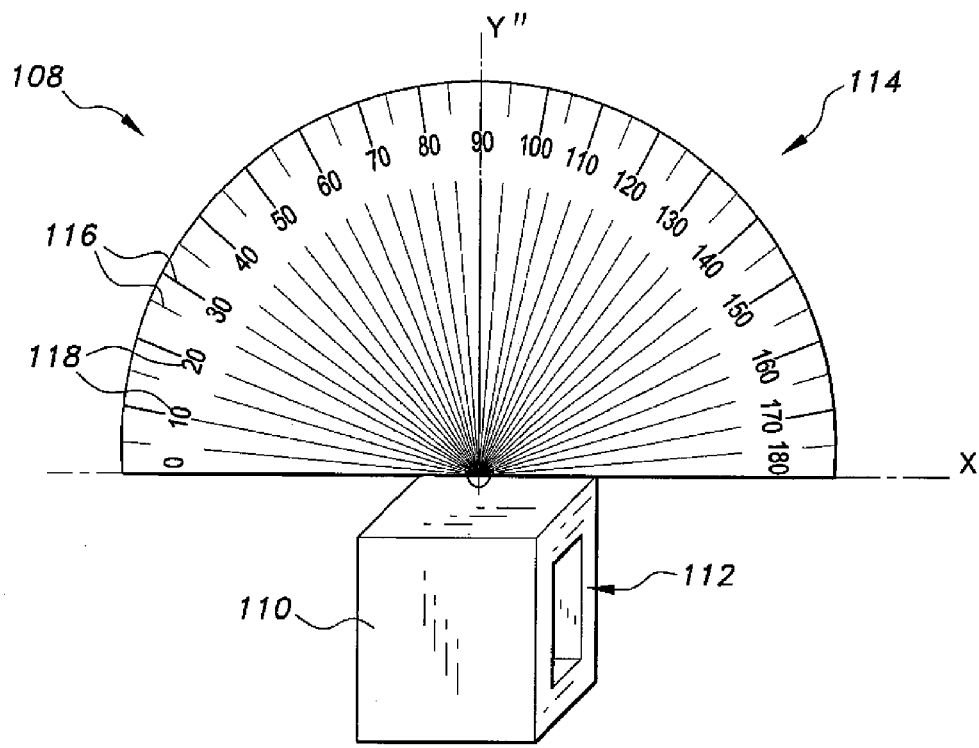
FIG. 3 is a front view of an embodiment of a measuring member of an embodiment of a dental implant angle measurement device according to the present invention.

Continuing with reference to FIG. 3, the measuring member 108 includes a base member 110. The base member 110 is capable of being movably positioned on the elongate member 106, such as by having a passage 112 that allows for the elongate member 106 to pass through the base member 110. The base member 110 can be of various suitable shapes, such as can allow for the passage 112 to receive the elongate member 106, and can allow for the base member 110 to be movably positioned along the elongate member 106. For example, the base member 110 of the measuring member 108 can have a square or generally square shape, as shown in FIG. 3. The base member 110 can have various suitable dimensions that allow for the base member 110 to be positioned within the mouth 160 of the patient, or to be positioned in relation to the cast 170. For example, the base member 110 can be 4 mm×4 mm and the passage 112 can be 2 mm×2 mm. Further, the base member 110 can have a wall thickness of 2 mm, for example. However, the dimensions of the base member 110 can be of various suitable dimensions, as can depend on the use or application, and should not be construed in a limiting sense.

An angular indicator 114 is positioned in conjunction with the base member 110 of the measuring member 108, for example by being mounted on the base member 110 as shown in FIG. 3. The angular indicator 114 of the measuring member 108 can be any suitable measurement device as, for example, a protractor, as shown in FIG. 3, among others, and should not be construed in a limiting sense. If a protractor is used for the angular indicator 114, the protractor can have any of various suitable dimensions, as can depend on the use or application. For example, the protractor can have a width of 20 mm.

The angular indicator 114 of the measuring member 108 can include gradations 116 corresponding to angular degrees to signify a value of an angle and to determine a corresponding angular difference of the $Y_2$ axis of the target dental component 150 relative to the $Y_1$ axis of the reference dental component 140. The angular indicator 114 can also have indicia 118 in addition to the gradations 116. The indicia 118, similar to the gradations 116, can be used to determine a corresponding angular difference of the target dental component 150 relative to the reference dental component 140. Thus, if a protractor is used as the angular indicator 114 for the measuring member 108, the protractor can include gradations 116 and/or indicia 118, for example.

The gradations 116 and/or the indicia 118 of the angular indicator 114 can be in a range from about 0 degrees to about 180 degrees, for example. Further, as shown in FIG. 3, the angular indicator 114 includes a Y" vertical axis that runs through the angle value of 90 degrees and further includes the X axis that runs through the 0 degree and 180 degrees values and that is parallel or substantially parallel to the elongate member 106. The X axis of the angular indicator 114 is not only perpendicular or substantially perpendicular to the Y" axis but is also perpendicular or substantially perpendicular to the Y' axis of the reference member 102. Thus, the X axis forming a 90 degree or substantially 90 degree angle between both the Y" and the Y' axes, respectively.

Further, the X axis is perpendicular or substantially perpendicular to the $Y_1$ axis of the reference dental component 140 when the dental implant angle measurement device 100 is placed in conjunction with the reference dental component 140 and the target dental component 150, thus forming a 90 degree or substantially 90 degree angle between both the X axis and the $Y_1$ axis of the reference dental component 140, for example.

The dental implant angle measurement device 100 also includes a stopping member 120. The stopping member 120 is positioned in conjunction with the elongate member 106 and is adapted to restrict movement of the measuring member 108 in relation to the elongate member 106. Thus, the stopping member 120 assists in preventing the measuring member 108 from losing contact with, or being separated from, the elongate member 106.

Referring to FIGS. 5A, 5B and 5C, the dental implant angle measurement device 100, as described, can be used within the oral cavity 164, such as the anterior portion or part 161 of the oral cavity 164 of the patient's mouth 160, or can be used in spatial relation 172 to the cast 170. The reference member 102 is adapted to be selectively positioned in substantial vertical alignment with the $Y_1$ axis passing through the reference dental component 140, with the reference dental component 140 being received by the lumen 104 of the reference member 102. Thus, the Y' axis of the reference member 102 can overlap and/or be aligned or substantially aligned with the $Y_1$ axis passing through the reference dental component 140, as shown in FIGS. 5B and 5C.

The measuring member 108 is adapted to be selectively positioned by the user for alignment or substantial alignment with the target dental component 150 so that the axis Y" passing through the measuring member 108 at the 90 degree or substantially 90 degree value of the angular indicator 114 is parallel or substantially parallel to the Y' axis passing through the reference member 102. The measuring member 108 when positioned in aligned relation, such as in alignment or substantial alignment, with the target dental component 150 determines an angular difference of the target dental component 150 relative to the reference dental component 140 by comparing the alignment of the $Y_2$ axis of the target dental component 150 with the Y" axis of the measuring member 108. Therefore, the angular position of the $Y_2$ axis relative to the position of the Y" axis is compared to determine if parallelism or substantial parallelism exists between the reference dental component 140 and the target dental component 150 by determining how the line of the $Y_2$ axis extending through the target dental component 150 aligns with the gradations 116 and/or indicia 118 of the angular indicator 114.

For parallelism or substantial parallelism between the reference dental component 140 and the target dental component 150 to exist, the line of the $Y_2$ axis extending through the target dental component 150 should align or substantially align with the Y" axis that is passing through the 90 degree or substantially 90 degree value of the angular indicator 114, or be close to the Y" axis. If too great of an angular difference exists, than parallelism or substantial parallelism is likely not present between the reference dental component 140 and the target dental component 150. If parallelism of substantial parallelism is not present between the reference dental component 140 and the target dental component 150, then the user can select an appropriate dental component to compensate for the misalignment, such as a nylon band, to be fitted with the target dental component 150 that is designated to compensate for the misalignment, for example.

The portions and structures of the dental implant angle measurement device 100, including the reference member 102, the elongate member 106, the measuring member 108, and the stopping member 120, can be made from various suitable materials that can allow for the dental implant angle measurement device 100 to be sterilized by common sterilization methods, for example by autoclave. Suitable materials can include, among others, stainless steel, such as medical grade stainless steel, for example.

It is to be understood that the present invention is not limited to the embodiments described above, but encompasses any and all embodiments within the scope of the following claims.

I claim:

1. A dental implant angle measurement device, comprising:
    a reference dental component;
    a reference member, the reference member being adapted to be positioned in engaging relation to the reference dental component, the reference dental component adapted to be positioned in a mouth of a patient;
    an elongate member, the elongate member positioned substantially perpendicular to and in conjunction with the reference member;
    a target dental component; and
    a measuring member, the measuring member being movably positioned in conjunction with the elongate member to selectively position the measuring member along the elongate member in an aligned relation with the target dental component, the target dental component adapted to be positioned in the mouth of the patient, wherein the measuring member includes an angular indicator having gradations corresponding to angular degrees,
    wherein the reference member and the elongate member are positioned in substantially perpendicular relation to one another, and the angular difference of the target dental component relative to the reference dental component is determined by the gradations of the measuring member.

2. The dental implant angle measurement device according to claim 1, wherein the dental implant angle measurement device is adapted to be positioned within an anterior part of an oral cavity of the mouth of the patient.

3. The dental implant angle measurement device according to claim 1, wherein the reference dental component and the target dental component each comprises an implant adapted to be positioned in a portion of the mouth of the patient.

4. The dental implant angle measurement device according to claim 3, wherein the each implant includes a post adapted to securely position the implant in the portion of the mouth of the patient.

5. The dental implant angle measurement device according to claim 1, wherein the angular indicator of the measuring member comprises a protractor.

6. The dental implant angle measurement device according to claim 5, wherein the protractor includes gradations in a range from about 0 degrees to about 180 degrees.

7. The dental implant angle measurement device according to claim 1, further comprising:
    a stopping member, the stopping member positioned in conjunction with the elongate member, the stopping member adapted to restrict movement of the measuring member in relation to the elongate member.

8. The dental implant angle measurement device according to claim 1, wherein
    the reference member is adapted to be selectively positioned in substantial vertical alignment with a first axis passing through the reference dental component, and
    the measuring member is adapted to be positioned in alignment with a second axis passing through the measuring member substantially parallel to the first axis passing through the reference member, the measuring member when positioned in substantial alignment with the target dental component determines the angular difference of the target dental component relative to the reference dental component, the angular difference being indicated by a third axis passing through the target dental component relative to a position of the second axis.

9. The dental implant angle measurement device according to claim 1, wherein
    the reference member comprises a lumen adapted to receive the reference dental component to selectively position the reference member in substantially vertical alignment with a first axis passing through the reference dental component, and
    the measuring member includes a base member and the angular indicator is positioned in conjunction with the base member and having the graduations to determine the corresponding angular difference of the target dental component relative to the reference dental component, a second axis passing through the base member and the angular indicator to position the base member and the angular indicator in substantially vertical alignment, the measuring member when positioned in substantial alignment with the target dental component determines the angular difference of the target dental component relative to the reference dental component, the angular difference being indicated by a third axis passing through the target dental component relative to a position of the second axis.

10. The dental implant angle measurement device according to claim 1, wherein the dental implant angle measurement device is comprised of a stainless steel material.

11. The dental implant angle measurement device according to claim 1, wherein the reference dental component and the target dental component are positioned in conjunction with a stone cast.

12. The dental implant angle measurement device according to claim 1, wherein the reference member includes a lumen adapted to receive the reference dental component.

13. A dental implant angle measurement device, comprising:

a reference dental component;

a reference member, the reference member having a lumen adapted to receive the reference dental component;

an elongate member, the elongate member positioned substantially perpendicular to and in conjunction with the reference member;

a target dental component; and a measuring member, the measuring member being movably positioned in conjunction with the elongate member to selectively position the measuring member along the elongate member in an aligned relation with the target dental component, the target dental component adapted to be positioned in the mouth of the patient, wherein the measuring member includes an angular indicator having gradations corresponding to angular degrees, wherein the reference member and the elongate member are positioned in substantially perpendicular relation to one another and in conjunction with a stone cast, the angular difference of the target dental component relative to the reference dental component is determined by the gradations of the measuring member.

* * * * *